United States Patent
Dekker et al.

(10) Patent No.: US 9,044,202 B2
(45) Date of Patent: Jun. 2, 2015

(54) SENSOR GUIDE WIRE

(71) Applicants: ST. JUDE MEDICAL SYSTEMS AB, Uppsala (SE); KONINKLIJKE PHILIPS ELECTRONICS N.V., Eindhoven (NL)

(72) Inventors: Ronald Dekker, Valkenswaard (NL); Vincent Adrianus Henneken, Utrecht (NL); Stefan Tiensuu, Uppsala (SE)

(73) Assignees: ST. JUDE MEDICAL COORDINATION CENTER BVBA, Zaventem (BE); KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 14/357,402
(22) PCT Filed: Oct. 26, 2012
(86) PCT No.: PCT/SE2012/051165
§ 371 (c)(1),
(2) Date: May 9, 2014
(87) PCT Pub. No.: WO2013/070146
PCT Pub. Date: May 16, 2013

(65) Prior Publication Data
US 2014/0288444 A1    Sep. 25, 2014

Related U.S. Application Data
(60) Provisional application No. 61/557,706, filed on Nov. 9, 2011.

(30) Foreign Application Priority Data
Nov. 9, 2011 (SE) ........................................ 1151051

(51) Int. Cl.
*A61B 5/00* (2006.01)
*A61M 25/09* (2006.01)
(52) U.S. Cl.
CPC .............. *A61B 5/6851* (2013.01); *A61M 25/09* (2013.01)

(58) Field of Classification Search
CPC ............... A61B 5/6851; A61M 25/09; A61M 2025/0166; A61M 5/1723
USPC .................................................. 600/561, 585
See application file for complete search history.

(56) References Cited

U.S. PATENT DOCUMENTS

| 5,095,401 A | 3/1992 | Zavracky et al. |
| 5,257,630 A | 11/1993 | Broitman et al. |

(Continued)

FOREIGN PATENT DOCUMENTS

| EP | 0 495 299 A1 | 11/1991 |
| EP | 1 016 430 A1 | 7/2000 |

OTHER PUBLICATIONS

International Search Report and Written Opinion, Jan. 31, 2013, 9 pages.

(Continued)

*Primary Examiner* — Max Hindenburg
(74) *Attorney, Agent, or Firm* — Foley & Lardner LLP (57) ABSTRACT

Sensor guide wire for intravascular measurements of physiological variables in a living body or of external signals, which sensor guide wire has a proximal region, a distal sensor region and a tip region, the sensor guide wire comprises a core wire having a longitudinal axis parallel to the longitudinal axis of the sensor guide wire, and a sensor element arranged in the distal sensor region, the sensor element has a sensitive portion for measuring the physiological variable and to generate a sensor signal in response to said variable. The sensor element has an essentially planar main surface and has its maximal extension in the plane of the main surface, and a thickness perpendicular to the plane of the main surface, wherein the sensor element is arranged in an essentially perpendicular relation to said core wire with regard to the planar main surface of the sensor element.

17 Claims, 4 Drawing Sheets

(56) References Cited

U.S. PATENT DOCUMENTS

| | | | |
|---|---|---|---|
| 5,510,276 A | 4/1996 | Diem et al. | |
| RE35,648 E | 11/1997 | Tenerz et al. | |
| 5,701,905 A * | 12/1997 | Esch | 600/486 |
| 5,836,886 A | 11/1998 | Itoigawa et al. | |
| 5,873,835 A | 2/1999 | Hastings et al. | |
| 6,131,466 A | 10/2000 | Vigna et al. | |
| 6,142,958 A * | 11/2000 | Hammarstrom et al. | 600/585 |
| 6,167,763 B1 | 1/2001 | Tenerz et al. | |
| 6,221,023 B1 | 4/2001 | Matsuba et al. | |
| 7,207,227 B2 | 4/2007 | Rangsten et al. | |
| 7,263,894 B2 * | 9/2007 | Tenerz | 73/756 |
| 7,967,761 B2 * | 6/2011 | Smith | 600/585 |
| 8,419,648 B2 * | 4/2013 | Corl et al. | 600/486 |
| 2007/0032744 A1 | 2/2007 | Lupton | |
| 2009/0088650 A1 | 4/2009 | Corl | |

OTHER PUBLICATIONS

International Preliminary Report on Patentability, May 13, 2014, 6 pages.

Swedish Office Action, Sep. 22, 2014, 5 pages.

* cited by examiner

SENSOR GUIDE WIRE

FIELD OF THE INVENTION

The present invention relates to a sensor guide wire for intravascular measurements of physiological variables in a living body, according to the preamble of the independent claim, and in particular to a sensor guide wire for intravascular pressure measurements.

BACKGROUND OF THE INVENTION

In many medical procedures, various physiological conditions present within a body cavity need to be monitored. These physiological conditions are typically physical in nature—such as pressure, temperature, rate-of-fluid flow, and provide the physician or medical technician with critical information as to the status of a patient's condition.

One device that is widely used to monitor conditions is the blood pressure transducer. A blood pressure transducer senses the magnitude of a patient's blood pressure, and converts it into a representative electrical signal that is transmitted to the exterior of the patient. For most applications it is also required that the sensor is electrically energized.

Some means of signal and energy transmission is thus required, and most commonly extremely thin electrical cables, sometimes called microcables, are provided inside a guide wire, which itself is provided in the form of a tube, which often has an outer diameter in the order of 0.35 mm, and oftentimes is made of steel.

In order to increase the bending strength of the tubular guide wire, a core wire is positioned inside the tube. The core wire also helps to improve "pushability" and "torquability" of the guide wire. The mentioned electrical cables are e.g. positioned in the space between the inner lumen wall and the core wire.

Sensor and guide wire assemblies in which a sensor is mounted at the distal end of a guide wire are known. In U.S. Pat. Re. 35,648, which is assigned to one of the present assignees, an example of such a sensor and guide wire assembly is disclosed, where a sensor and guide wire assembly comprises a sensor element, an electronic unit, a signal transmitting cable connecting the sensor element to the electronic unit, a flexible tube having the cable and the sensor element disposed therein, a solid metal wire, and a coil attached to the distal end of the solid wire. The sensor element comprises a pressure sensitive device, typically a membrane, with piezoresistive elements connected in a Wheatstone bridge-type of arrangement mounted thereon.

As is disclosed in, for example, U.S. Pat. No. 6,167,763, which also is assigned to one of the present assignees, the sensor element can be arranged inside a short tube (usually referred to as a sleeve or jacket), which protects the sensor element and comprises an aperture through which the pressure sensitive device is in contact with the ambient medium. The solid metal wire—which, as also mentioned above, in the art usually is referred to as the core wire—extends through the interior of the jacket and may be provided with an enlarged diameter portion adapted for mounting of the sensor element.

The entire contents of all of the above-described documents are incorporated herein by reference for the methods and devices described therein.

A potential problem with this kind of guide wire mounted sensors is the occurrence of so-called bending artefacts. A bending artefact is a change in the output signal from the sensor that is induced by a bending of the guide wire, rather than being induced by a change in the physical environment surrounding the sensor.

To achieve the desired resistance against bending artefacts, the sensor may be designed and mounted in different ways, the common feature being that it is a cantilevered mounting arrangement that provides the desired resistance against bending artefacts.

The cantilevered mounting of the sensor, however, requires extra machining or wire forming of the core wire at the site where the sensor chip is placed. The careful machining of the core wire into different diameters and different shapes at different portions of the guide wire is a time-consuming process and may be a source of manufacturing mistakes, leading to loss of time and material in the manufacturing process.

In U.S. Pat. No. 6,221,023 is disclosed a sensor mounted on the distal end of an intra-corporal catheter. The sensor includes a chip that is deformable in accordance with pressure applied thereto, strain gauges mounted on the chip, a sensing plate, a projection, a cap and a tube. The projection and the cap transmit pressure applied to the catheter's distal end to the sensing plate and tilt the sensing plate in accordance with the pressure where the strain gauges issue detection signals according to the degree and the direction of the tilting.

The inventors have realized that there is a need for a sensor guide wire wherein the mounting of the sensor does not involve extra machining or wire forming, which thereby is easier and less expensive to manufacture. In addition, a further need is to improve the resistance to bending artefacts, and also to improve the flexibility and bending profile of the distal portion of the sensor guide wire.

SUMMARY OF THE INVENTION

The above-mentioned object is achieved by the present invention according to the independent claim.

Thus, the present invention relates to a sensor guide wire for intravascular measurements of physiological variables in a living body or of external signals, which sensor guide wire has a proximal region, a distal sensor region and a tip region. The sensor guide wire comprises a core wire having a longitudinal axis parallel to the longitudinal axis of the sensor guide wire, and a sensor element arranged in the distal sensor region, the sensor element has a sensitive portion for measuring the physiological variable, or external signal, and to generate a sensor signal in response to said variable/signal. The sensor element has an essentially planar main surface and has its maximal extension in the plane of the main surface, and a thickness perpendicular to the plane of the main surface, wherein the sensor element is arranged in an essentially perpendicular relation to the core wire with regard to the planar main surface of the sensor element.

In a preferred embodiment the sensor element is provided with a through-going opening in the perpendicular direction with regard to the main surface. The sensor element is mounted in relation to the core wire such that the core wire extends through the through-going opening and such that the plane of the sensor element is essentially perpendicular to the longitudinal axis of the core wire.

The present invention is based upon the insight by the inventors who have realized that the stiff section of the core wire of a conventional pressure wire having the sensor element mounted in a cantilever fashion is approximately 2 mm which reduces the flexibility of the pressure sensor wire. By reducing the longitudinal extension of the stiff section of the core wire the flexibility performance is improved.

By the present invention an improved sensor guide wire is achieved which has a stiff section of the core wire in relation to the sensor element which is considerably shorter in comparison to the presently used sensor guide wire which results in a more flexible distal part of the sensor guide wire. In addition, the longitudinal extension of the jacket, arranged to protect the sensor element, may be considerably reduced which further improves the flexibility of the distal part of the sensor guide wire. As one example the longitudinal extension of the jacket may be reduced from 2.25 mm to 1.1 mm. The ability to insert the sensor guide wire into the tortuous cardiac veins is thereby improved. This is further illustrated by FIG. 11.

Figure 7:
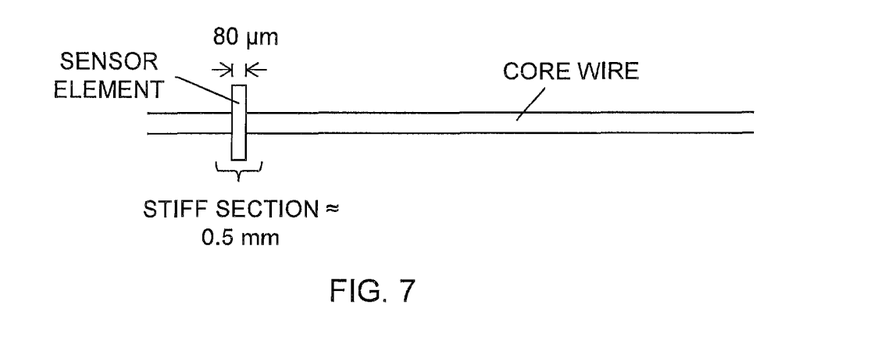
FIG. 7 is side view illustrating the present invention.

According to one embodiment the stiff section is approximately in the range of 0.3-0.5 mm. Generally the stiff section is related to the thickness of the sensor element (and also the longitudinal extension of the jacket) which preferably is in the range of 60-200 µm, preferably 80 µm. This is illustrated by FIG. 7 showing a schematic side view of the core wire having the sensor element mounted in accordance with the present invention.

DETAILED DESCRIPTION OF PREFERRED EMBODIMENTS OF THE INVENTION

Throughout the application the word distal means distal in respect to the operator of the sensor guide wire and proximal means proximal in respect to the operator.

Figure 1:
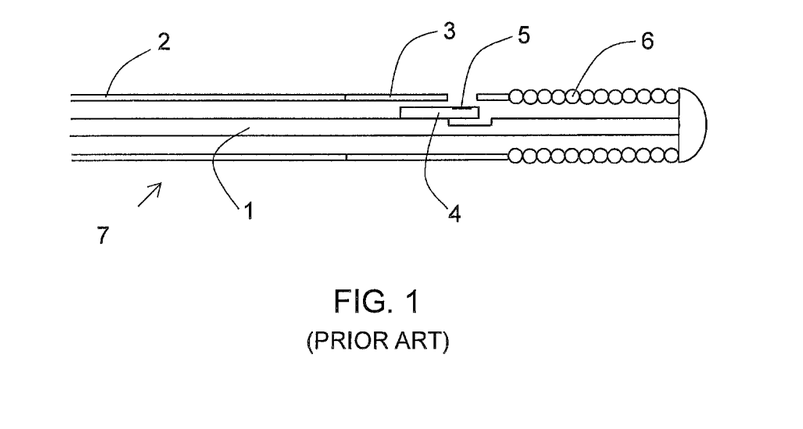
FIG. 1 illustrates the distal end of a sensor guide wire according to the prior art.

FIG. 1 illustrates the distal part of a sensor guide wire 7 according to the prior art, see e.g. the above-mentioned U.S. Pat. No. 6,167,763. The sensor guide wire 7 comprises a core wire 1, a hollow tube 2, a hollow jacket 3, a sensor element 4 with a sensitive portion 5, e.g. a pressure sensitive portion, and a coil 6. The core wire 1 is at least partly disposed inside the hollow tube 2 and extends through the jacket 3 and into the coil 6. The sensor element 4, comprising the sensitive portion 5, is mounted on the core wire 1 within the jacket 3, and is connected to an electronic unit (not shown in the figure) via one or several electrical leads, e.g. so-called microcables (not shown in the figure).

Figure 2:
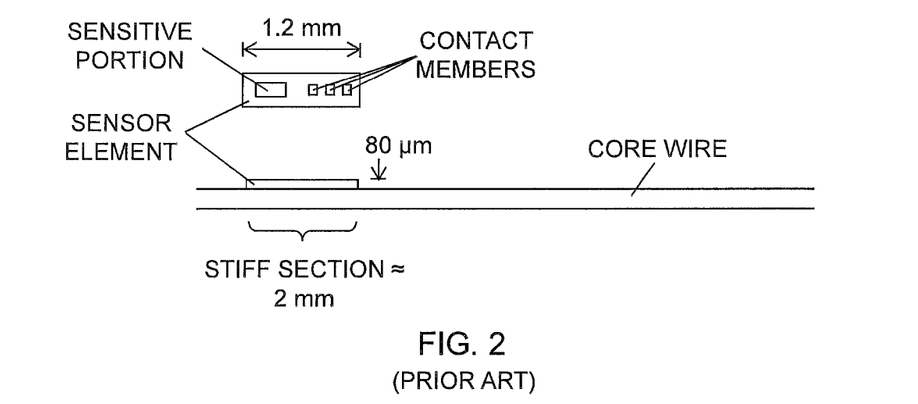
FIG. 2 is a schematic side view of a core wire and a sensor element according to prior art.

FIG. 2 is a schematic side view of a core wire and a sensor element according to prior art. In the figure the distal end of the core wire is disclosed provided with a sensor element, e.g. in the form of a rectangular chip which is approximately 1.2 mm long and 80 µm thick. The sensor element includes a sensitive portion and a number of contact elements for connection to microcables. The sensor element is normally enclosed in a jacket which is obviated in the figure for sake of simplicity. As discussed in the background section this known construction results in a rather long stiff section of the sensor guide wire which might cause bending artefacts of the sensor element that could influence the measurement accuracy.

Figure 3:
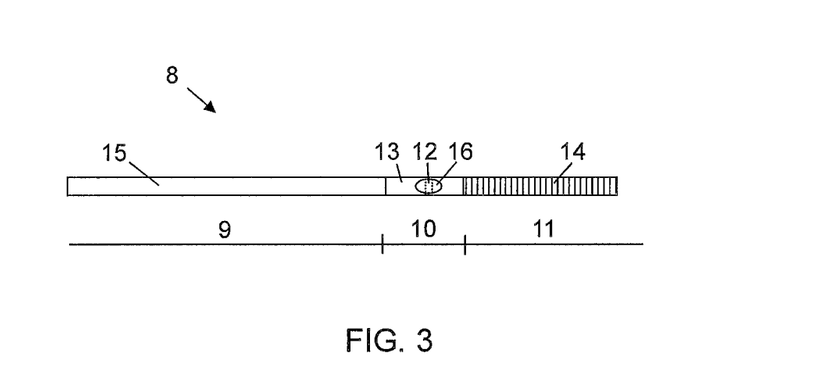
FIG. 3 is a schematic side view of a sensor guide wire according to the present invention.

In FIG. 3 is disclosed a side view of a sensor guide wire 8 for intravascular measurements of physiological variables, or externally generated signals, e.g. electrical and/or magnetic field signals, in a living body according to the present invention, having a proximal region 9, a distal sensor region 10 and a tip region 11. The sensor guide wire 8 comprises a core wire (not shown) having a longitudinal axis parallel to the longitudinal axis of the sensor guide wire, a sensor element 12 arranged in the distal sensor region, which has a sensitive portion (not shown), e.g. a pressure sensitive portion, for measuring the physiological variable, or the external signal, and to generate a sensor signal in response of the variable/external signal, and a jacket 13, accommodating at least a portion of the sensor element 12. At least one signal transmitting microcable (not shown) may be connected to the sensor element 12, and running along the sensor guide wire 8. The sensor guide wire 8 further comprises a coil 14 arranged in the tip region 11 and a hollow tube 15 at least partly enclosing the signal transmitting microcable(s), in the proximal region 9. According to this preferred embodiment, the jacket 13 is provided with a jacket opening 16 in the sensor region 10, at the site where the pressure sensitive portion is arranged.

Figure 4:
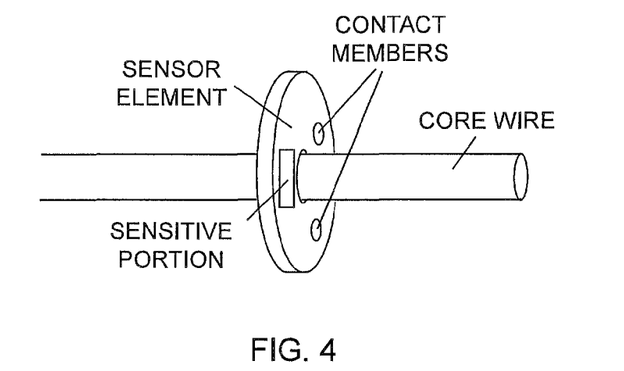
FIG. 4 is a perspective view illustrating a first embodiment of the present invention.

FIG. 4 is a perspective view illustrating the present invention. In the figure only the core wire and the sensor element are shown in order to fully illustrate the invention.

The sensor element has an essentially planar main surface and has its maximal extension in the plane of the main surface, and a thickness perpendicular to the plane of the main surface, wherein the sensor element is arranged in an essentially perpendicular relation to the core wire with regard to the planar main surface of the sensor element.

The sensor element is provided with a through-going opening in the perpendicular direction with regard to the main surface, wherein the sensor element is mounted in relation to the core wire such that said core wire extends through said through-going opening and such that the plane of the sensor element is essentially perpendicular to the longitudinal axis of the core wire.

The angle between the planar main surface and the axis of the core wire is in the range of 80-100 degrees.

Figure 5:
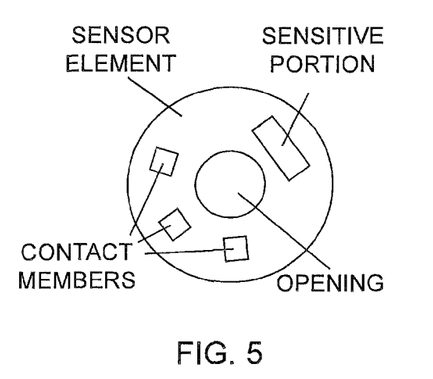
FIG. 5 is a top view of a sensor element according to a first embodiment of the present invention.

According to a first embodiment the through-going opening is a hole, preferably a circular hole which is illustrated in FIGS. 4 and 5.

FIG. 5 is a top view of the sensor element according to the first embodiment. In this embodiment the sensor element is provided with a circular hole for receiving the core wire, a sensor portion and a number of contact members including contact elements for establishing electrical connection to one or many micro-cables. In the illustrated sensor element three contact members are included.

Figure 6:
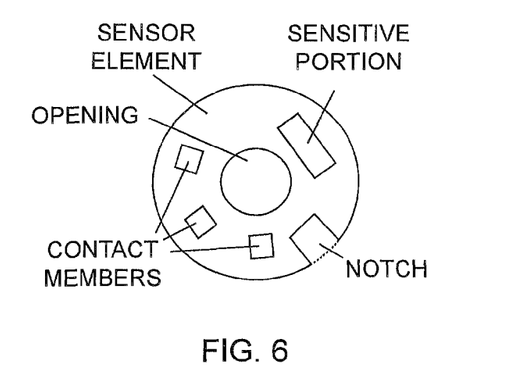
FIG. 6 is a top view of a sensor element illustrating a modified first embodiment of the present invention.

According to another embodiment a notch in the periphery of the sensor element is arranged such that the micorcables may pass the sensor element and an electrical connection may be provided at the distal side of the sensor element. This embodiment is illustrated by FIG. 6. This embodiment simplifies the mounting procedure in that the sensor element may be horizontally arranged when the microcables are connected (by e.g. fusing or soldering) to the contact elements and the sensor element is then turned to a vertical position in relation to the core wire and the insulated microcables pass to the distal side via the notch. The arrangement of a notch in the periphery of the sensor element allowing the microcables to pass the sensor element may be applied to all embodiments described herein, wherever it is applicable. The notch is illustrated in FIG. 6, and also in FIG. 10.

The present invention is also applicable in embodiments where the communication between the sensor element and an external unit is wireless. In that case the sensor element is provided with a processing and transmitting unit adapted to process the measured physiological signal and to transmit the processed signal to the external unit. In that case no contact members are required.

Figure 8:
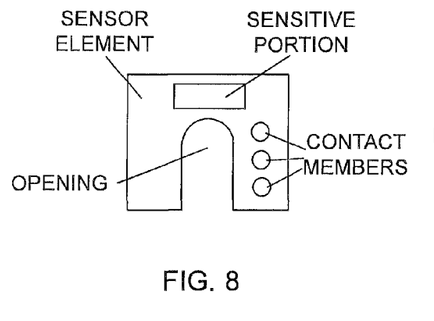
FIG. 8 is a top view illustrating a second embodiment of the present invention.
Figure 9:
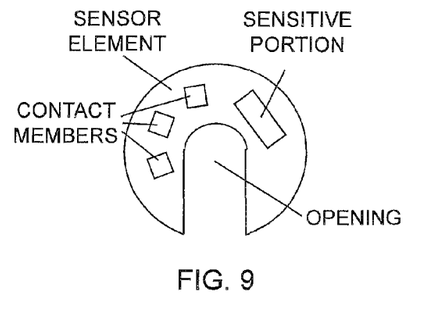
FIG. 9 is a top view illustrating a third embodiment of the present invention.

According to a second and a third embodiment of the present invention, which are illustrated by FIGS. 8 and 9, the through-going opening is a radial slit having a predetermined width related to the width of the core wire extending from the periphery to the centre of the sensor element. The width is such that the core wire easily may be arranged within the slit. One advantage with these embodiments is that the manufacturing and mounting processes are simplified. Another advantage is that the microcables also may be arranged in the radial slit. In that regard the core wire is first arranged and the microcables are then arranged in the remaining space in the radial slit between the core wire and the sensor element periphery.

The second embodiment is illustrated in FIG. 8 where the sensor element has a square peripheral shape where the slit extends from one of the sides to the centre of the sensor element.

The third embodiment is illustrated in FIG. 9 where the sensor element has a circular peripheral shape where the slit extends from the side to the centre of the sensor element.

Figure 10:
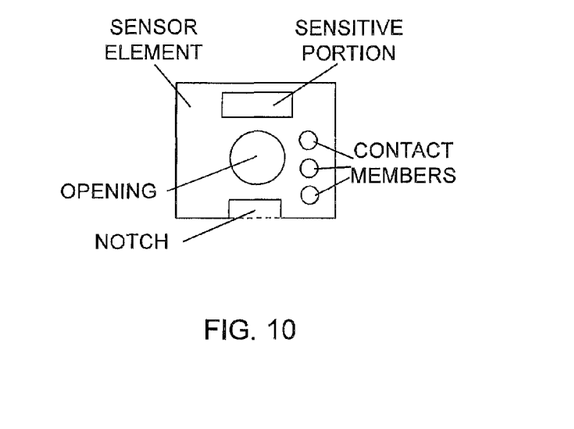
FIG. 10 is a top view illustrating a fourth embodiment of the present invention.
Figures 11A, 11B, 11C, 11D:
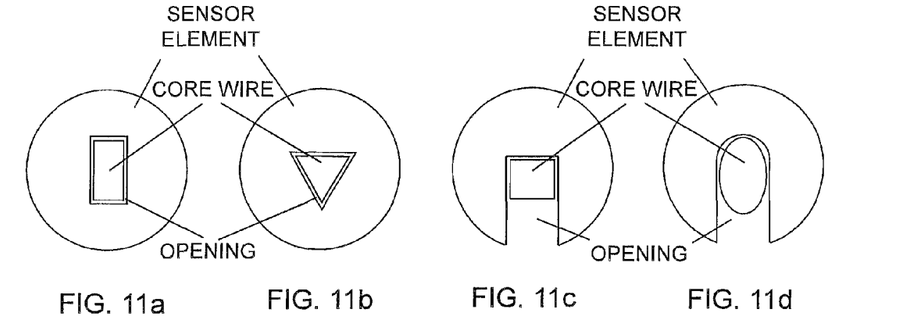
FIGS. 11a-11d are top views of a circular sensor element schematically illustrating different cross-sectional shapes of the core wire and opening.
Figures 12A, 12B:
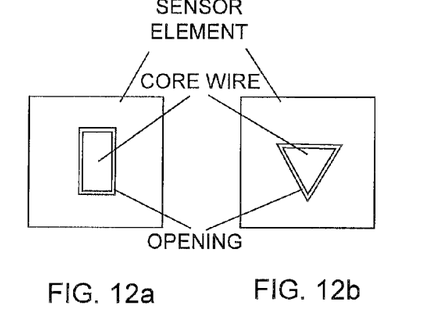
FIGS. 12a-12d are top views of a rectangular sensor element schematically illustrating different cross-sectional shapes of the core wire and opening.
Figures 12C, 12D:
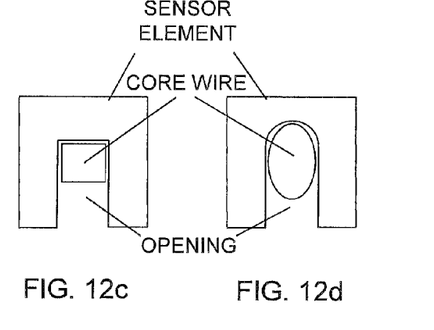

FIG. 10 is a top view illustrating a fourth embodiment of the present invention where the sensor element has a rectangular peripheral shape and is provided with a notch on one of its sides where the microcables are arranged such that they then pass the sensor element and provide for connection to the contact members at the distal side of the sensor element.

Thus, the planar main surface of the sensor element has a circular or elliptical shape, or as an alternative, the planar main surface of said sensor element has a rectangular or square shape. These shapes are applicable for all embodiments described herein. Naturally, within the scope of the present invention as defined by the claims, other shapes are possible, e.g. triangular, or non-symmetrical shapes.

The through-going opening has a size such that said core wire extends through the opening when the sensor element is mounted on the core wire.

FIGS. 11a-11d are top views of a circular sensor element schematically illustrating different cross-sectional shapes of the core wire and opening.

FIGS. 12a-12d are top views of a rectangular sensor element schematically illustrating different cross-sectional shapes of the core wire and opening.

According to the embodiments illustrated in FIGS. 11a-11d and 12a-12d the cross-sectional shape of the opening is adapted to the cross-sectional shape of core wire where the sensor element is to be arranged. Thereby the sensor element may be safely positioned, e.g. rotation is obviated. Another advantage is that the mounting of the sensor element is simplified in that that the cross-sectional shape of the opening and corewire can be chosen such that there is only one way to mount the sensor element at the core wire.

In the figures the core wire is given a rectangular, a triangular, a square and an elliptical shape, respectively. The cross-sectional shape of the core wire may be achieved e.g. by grinding and is preferably made only where the sensor element should be mounted.

Advantageously, the opening for the core wire, or the radial slit and/or the notch are etched. Other manufacturing methods are naturally possible within the scope of the present invention. Below, a Silicon-On-Insulator (SOI) manufacturing method will briefly be described which method is applicable when manufacturing the sensor element according to the present invention.

Preferably, the sensor element is mounted such that the sensitive portion faces the distal direction of the sensor guide wire. It is also possible to mount the sensor element such that the sensitive portion faces the proximal direction of the sensor guide.

Advantageously, the sensor element is attached to the core wire by glue, or by welding or soldering.

The sensor element is adapted to measure one or many of the physiological variables pressure, temperature, flow. In addition the sensor element may be adapted to measure external signals, such as electromagnetic signals, magnetic signals, radio signals, etc, e.g. to determine the position of the sensor element.

The maximal extension of the sensor element is at least three times larger than the thickness. The outer diameter of the core wire is preferably in the range of 60-200 µm, the thickness of the sensor element is less than 100 µm, preferably 80 µm and the maximal extension of the sensor element is in the range of 300-400 µm, preferably 360 µm.

Pressure sensors, which is one preferred application of the sensor wire according to the present invention, used in the context of measuring intracoronary pressure often contain a deflectable diaphragm. The two main types of such pressure sensors are absolute pressure sensors and differential or relative pressure sensors. In an absolute pressure sensor the diaphragm is usually mounted across a small cavity wherein a reference pressure, usually vacuum pressure, exists, and the pressure to be measured acts on the opposing surface of the diaphragm. A differential pressure sensor measures the difference of two pressures acting on opposing sides of the diaphragm.

The movement or deformation of the diaphragm can be sensed in different ways, such as by measuring the changes of electric characteristics of a piezoresistive body, the changes of resistance of an electrical conductor or the change of capacitance of a suitable adapted capacitor coupled to the movement of the diaphragm and thereby being in varied forced or strained states.

Absolute pressure sensors need a hermetic sealing of a relatively small cavity at the active diaphragm to get a reference pressure, preferably a vacuum enclosure. This can be accomplished on a wafer using e.g. silicon wafer bonding under vacuum conditions.

Generally, for example for use in a sensor guide wire as described above, a small piezoresistive absolute pressure sensor is desired, having a high pressure sensitivity, a controlled temperature behaviour and a high long term stability. It should not be affected by environmental changes, such as humidity or possible temperature fluctuations. Also, a manufacturing process suitable for high volume production and with a high yield is preferred.

Recently, micromachining techniques have been developed and refined for producing integrated miniaturized pressure sensors of semiconductor material, providing several advantages over traditional pressure sensors: low cost, high degree of performance and reliability, better signal/noise ratio, and greater reproducibility.

Several pressure sensors based on silicon-on-insulator (SOI) substrates have been proposed. For example, U.S. Pat. Nos. 6,131,466, 5,510,276, 5,095,401, and 7,207,227, disclose such sensors. In U.S. Pat. No. 7,207,227, a method of manufacturing a pressure sensor is described, wherein a cavity is formed in an SOI substrate, and thereafter a second silicon wafer is bonded to the first to seal the cavity. After several etching and deposition steps, a sensor complete with electrical strain gauge is produced.

Figures 13, 14:
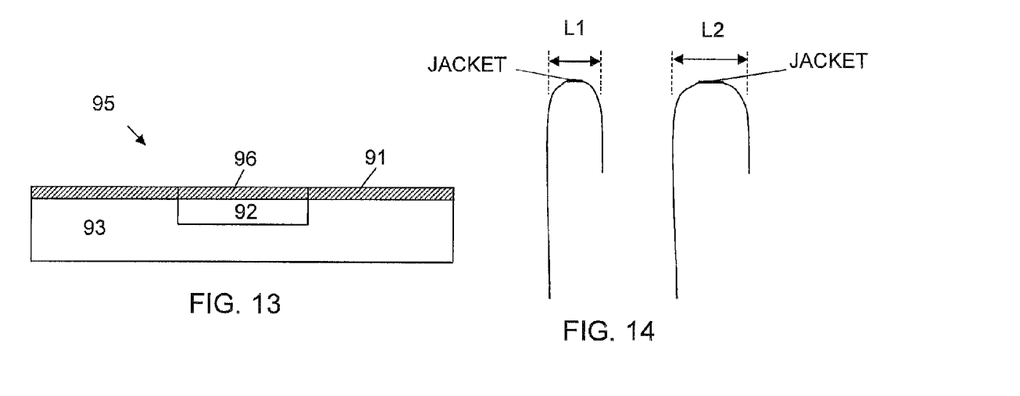
FIG. 13 is a cross-sectional view schematically illustrating a pressure sensor according to prior art.
FIG. 14 illustrates the improved flexibility of the distal part of the sensor guide wire according to the present invention.

FIG. 13 is a schematic cross-sectional view illustrating a conventional pressure sensor chip 95 (that corresponds to the sensor element referred to in the present application) based on an SOI substrate. The pressure sensor chip 95 includes a crystalline silicon substrate 93, a cavity recess 92 formed in the crystalline silicon substrate 93, and a crystalline silicon layer 91 forming a diaphragm 96 over the cavity recess 92. A certain pressure exerted on the diaphragm 96 from the surrounding medium will thereby correspond to a certain stretching of the diaphragm 96 and thereby to a certain resistance of piezoresistive elements (not shown in FIG. 10), disposed on the diaphragm.

FIG. 14 illustrates the improved flexibility of the distal part of the sensor guide wire according to the present invention. In the figure the distal portion of the sensor wire is schematically shown; the left illustration shows the distal part according to the present invention where the short stiff portion of the jacket, approximately 1.1 mm, improves the flexibility in comparison to the presently used sensor guide wire, which is illustrated by the right illustration, where the stiff portion is considerably longer. In the figure the maximal bending of the sensor guide wires are shown and the lengths L1 and L2 (which are related to the bending radius) are indicated, which very clearly illustrate the improved flexibility and ability to easily insert the guide wire into tortuous vessels.

Figure 15:
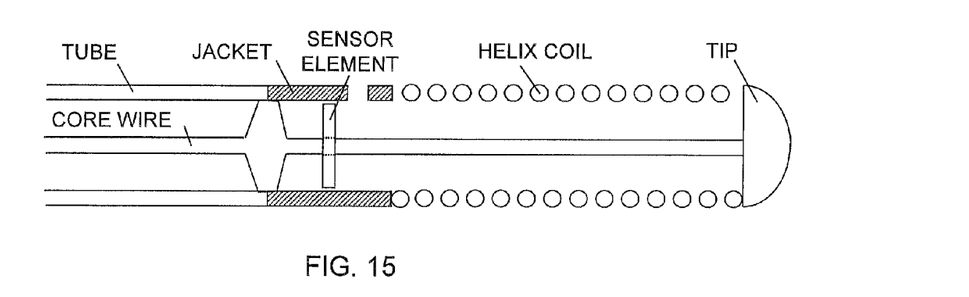
FIG. 15 shows a side view of the distal portion of a sensor guide wire according to the present invention.

And finally, FIG. 15 shows a side view of the distal portion of a sensor guide wire according to the present invention. The core wire is provided with a short portion where the diameter is increased where the jacket and a proximal tube is attached to the core wire. In the figure is also shown the sensor element being protected by the jacket, having a typical longitudinal extension of 1-1.5 mm, preferably 1.1 mm. The jacket is provided with an opening through which the sensor element is brought into contact with e.g. the blood. The most distal part of the sensor guide wire is preferably provided with a flexible helix wounded coil and a protective tip.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A sensor guide wire for intravascular measurement of a physiological variable in a living body or of an external signal, the sensor guide wire comprising:
 a proximal region, a distal sensor region, and a tip region;
 a core wire extending longitudinally through at least a portion of the sensor guide wire;
 a sensor element located in the distal sensor region, the sensor element having a sensitive portion configured to measure the physiological variable or external signal, and the sensor element being configured to generate a sensor signal in response to the physiological variable or the external signal;
 wherein the sensor element has an essentially planar main surface that extends in a plane that is essentially perpendicular to a longitudinal axis of the sensor guide wire,
 wherein the sensor element includes an opening through which the core wire extends in a longitudinal direction of the sensor guide wire, and
 wherein the sensor element is mounted such that the sensitive portion faces the longitudinal direction of the sensor guide wire.

2. The sensor guide wire of claim 1, wherein the sensor element is a pressure sensor.

3. The sensor guide wire of claim 1, wherein an angle between the planar main surface of the sensor element and the longitudinal axis of the sensor guide wire is in a range of 80-100 degrees.

4. The sensor guide wire of claim 1, wherein the opening of the sensor element is a hole.

5. The sensor guide wire of claim 1, wherein the opening of the sensor element is a radial slit extending from a periphery of the sensor element to a center of the sensor element.

6. The sensor guide wire of claim 1, wherein a length of the sensor element in a radial direction of the sensor guide wire is at least three times larger than a thickness of the sensor element in the longitudinal direction of the sensor guide wire.

7. The sensor guide wire of claim 1, wherein a cross-sectional shape of the core wire in the vicinity of the opening is adapted to a cross-sectional shape of the opening, such that rotation of the sensor element relative to the core wire is inhibited.

8. The sensor guide wire of claim 1, wherein an outer diameter of the core wire is in a range of 60-200 μm, a thickness of the sensor element in a longitudinal direction of the sensor guide wire is less than 100 μm, and a length of the sensor element in a radial direction of the sensor guide wire is in a range of 300-400 μm.

9. The sensor guide wire of claim 1, wherein the sensor guide wire further comprises a jacket accommodating at least a portion of the sensor element, the jacket including an opening enabling the sensitive portion to measure the physiological variable.

10. The sensor guide wire of claim 9, wherein the jacket has a length in the longitudinal direction of the sensor guide wire in a range of 1-1.5 mm.

11. The sensor guide wire of claim 1, wherein the sensor element is mounted such that the sensitive portion faces a distal direction of the sensor guide wire.

12. The sensor guide wire of claim 1, wherein the sensor element includes one or more contact members configured to establish electrical connection to one or more micro-cables.

13. The sensor guide wire of claim 1, wherein the planar main surface of the sensor element has a circular shape.

14. The sensor guide wire of claim 1, wherein the planar main surface of the sensor element has an elliptical shape.

15. The sensor guide wire of claim 1, wherein the planar main surface of the sensor element has a square or rectangular shape.

16. The sensor guide wire of claim 1, wherein the sensor element includes at least one notch formed in a periphery of the sensor element, the at least one notch being configured to allow one or more micro-cables to pass through the sensor element in the longitudinal direction of the sensor guide wire.

17. The sensor guide wire of claim 1, wherein the sensor element is attached to the core wire by glue.

* * * * *